US011504177B2

(12) United States Patent
Lin et al.

(10) Patent No.: US 11,504,177 B2
(45) Date of Patent: Nov. 22, 2022

(54) MANUFACTURING METHOD FOR BONE IMPLANT

(71) Applicant: INDUSTRIAL TECHNOLOGY RESEARCH INSTITUTE, Hsinchu (TW)

(72) Inventors: Cen-Ying Lin, Kaohsiung (TW); Sung-Ho Liu, Kaohsiung (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 372 days.

(21) Appl. No.: 16/807,557

(22) Filed: Mar. 3, 2020

(65) Prior Publication Data

US 2020/0197062 A1 Jun. 25, 2020

Related U.S. Application Data

(62) Division of application No. 14/985,381, filed on Dec. 30, 2015, now Pat. No. 10,603,093.

(30) Foreign Application Priority Data

Dec. 1, 2015 (TW) .................. 104140192

(51) Int. Cl.
*A61B 17/86* (2006.01)
*A61B 17/84* (2006.01)

(52) U.S. Cl.
CPC .......... *A61B 17/866* (2013.01); *A61B 17/846* (2013.01); *A61B 17/8625* (2013.01)

(58) Field of Classification Search
CPC ....... A61B 17/86; A61B 17/866; A61B 17/84; A61B 17/846; A61B 17/8625; C23C 14/34; B29C 59/16
See application file for complete search history.

(56) References Cited

U.S. PATENT DOCUMENTS

| 5,667,385 A | 9/1997 | Hansson |
| 6,102,703 A | 8/2000 | Day |
| 6,419,491 B1 | 7/2002 | Ricci et al. |
| 6,454,569 B1 | 9/2002 | Hollander et al. |

(Continued)

FOREIGN PATENT DOCUMENTS

| CN | 201743790 U | 2/2011 |
| TW | 491714 B | 6/2002 |

(Continued)

OTHER PUBLICATIONS

Ganeles, Jeffrey et al.; "Immediate and early loading of Straumann implants with a chemically modified surface (SLActive) in the posterior mandible and maxilla: 1-year results from a prospective multicenter study"; Clin. Oral Impl. Res. 19, 2008; pp. 1119-1128.

(Continued)

*Primary Examiner* — Christopher J Beccia
(74) *Attorney, Agent, or Firm* — Rabin & Berdo, P.C.

(57) ABSTRACT

A manufacturing method for a bone implant is provided. The manufacturing method includes the following steps. Firstly, an implant body is provided, wherein the implant body is made of metal comprising titanium or an alloy comprising titanium. Then, a processing apparatus is provided, wherein the processing apparatus comprises an ultrafast laser source, a first wave plate and a second wave plate. Then, ultrafast laser light is emitted by the ultrafast laser source to the implant body through the first wave plate and the second wave plate to form a plurality of microstructures and a titanium dioxide film, wherein each microstructure has a height and a weight, the weight is less than 2 micrometers, and the height is less than 1 micrometer.

5 Claims, 3 Drawing Sheets

(56) References Cited

U.S. PATENT DOCUMENTS

| | | | |
|---|---|---|---|
| 7,048,541 B2 | 5/2006 | Hall et al. | |
| 7,087,085 B2 | 8/2006 | Steinemann et al. | |
| 7,169,317 B2 | 1/2007 | Beaty | |
| 8,956,637 B2 | 2/2015 | Dubrow et al. | |
| 10,603,093 B2 * | 3/2020 | Lin | A61B 17/866 |
| 2001/0039454 A1 | 11/2001 | Ricci et al. | |
| 2005/0119758 A1 | 6/2005 | Alexander et al. | |
| 2005/0218315 A1 * | 10/2005 | Li | B23K 26/064 250/234 |
| 2008/0220394 A1 | 9/2008 | Berckmans et al. | |
| 2012/0046732 A1 * | 2/2012 | Sillekens | A61L 31/022 420/409 |
| 2012/0095555 A1 * | 4/2012 | Hsieh | A61C 8/0015 205/333 |
| 2012/0258428 A1 | 10/2012 | Molz | |
| 2012/0303127 A1 | 11/2012 | Ullrich, Jr. et al. | |
| 2012/0312779 A1 | 12/2012 | Patterson et al. | |
| 2012/0316650 A1 | 12/2012 | Ullrich, Jr. et al. | |
| 2012/0316651 A1 | 12/2012 | Ullrich, Jr. et al. | |
| 2013/0292357 A1 | 11/2013 | Ullrich, Jr. et al. | |
| 2013/0304218 A1 | 11/2013 | Ullrich, Jr. et al. | |
| 2013/0306591 A1 | 11/2013 | Ullrich, Jr. et al. | |
| 2014/0093842 A1 | 4/2014 | Strong et al. | |
| 2014/0094921 A1 | 4/2014 | Patterson et al. | |
| 2015/0018958 A1 | 1/2015 | Ullrich, Jr. et al. | |

FOREIGN PATENT DOCUMENTS

| | | |
|---|---|---|
| TW | 201244700 A | 11/2012 |
| TW | M447219 U | 2/2013 |
| TW | 201315846 A | 4/2013 |
| TW | I394559 B | 5/2013 |
| TW | 201320971 A | 6/2013 |
| TW | 201402062 A | 1/2014 |
| TW | I462757 B | 12/2014 |
| TW | 201509433 A | 3/2015 |
| WO | 2014072507 A1 | 5/2014 |

OTHER PUBLICATIONS

Mendonça, Gustavo et al.; "Advancing dental implant surface technology—From micron-to nanotopography"; Biomaterials 29 (2008) pp. 3822-3835; available online Jul. 9, 2008 in Biomaterials (www.elsevier.com/locate/biomaterials).

Nevins, Myron et al.; "Histologic Evidence of a Connective Tissue Attachment to Laser Microgrooved Abutments: A Canine Study"; The International Journal of Periodontics & Restorative Dentistry; vol. 30, No. 3, 2010; pp. 245-255.

Schätzle, Marc et al.; "Stability change of chemically modified sandblasted/acid-etched titanium palatal implants. A randomnized-controlled clinical trial"; Clin. Oral Impl. Res. 20, 2009; pp. 489-495.

Schwarz, Frank et al.; "Potential of Chemically Modified Hydrophilic Surface Characteristics to Support Tissue Integration of Titanium Dental Implants"; Journal of Biomedical Materials Research, Part B: Applied Biomaterials; Published online Oct. 6, 2008 in Wiley InterScience (www.interscience.wiley.com).

Taiwanese Office Action dated Jan. 15, 2016.

* cited by examiner

MANUFACTURING METHOD FOR BONE IMPLANT

This application claims the benefit of Taiwan application Serial No. 104140192, filed Dec. 1, 2015, the disclosure of which is incorporated by reference herein in its entirety, and this application is a divisional application of co-pending application Ser. No. 14/985,381, filed Dec. 30, 2015, the contents of which are incorporated herein by reference.

TECHNICAL FIELD

The disclosure relates to a manufacturing method for a bone implant.

BACKGROUND

After a bone implant, such as a bone screw, is implanted into a bone, bone tissue climbs the bone implant to grow for speeding up the healing of the bone. However, a surface of a bone implant is smooth, and thus it is not easy for the bone tissue to climb the surface of the bone implant, such that healing for the bone tissue is slow.

Accordingly, there is a need for a bone implant to be conducive to the climbing of the bone tissue.

SUMMARY

The disclosure provides a manufacturing method for a bone implant.

According to another embodiment, a manufacturing method of the bone implant is provided. The method includes the following steps. An implant body is provided, wherein the implant body is made of metal comprising titanium or an alloy comprising titanium; a processing apparatus is provided, wherein the processing apparatus comprises an ultrafast laser source, a first wave plate and a second wave plate; and ultrafast laser light is emitted by the ultrafast laser source to the implant body through the first wave plate and the second wave plate to form a plurality of microstructures and a titanium dioxide film, wherein each microstructure has a height and a weight, the weight is less than 2 micrometers, and the height is less than 1 micrometer.

The above and other aspects of the disclosure will become better understood with regard to the following detailed description of the preferred but non-limiting embodiment (s). The following description is made with reference to the accompanying drawings.

Figure 1:
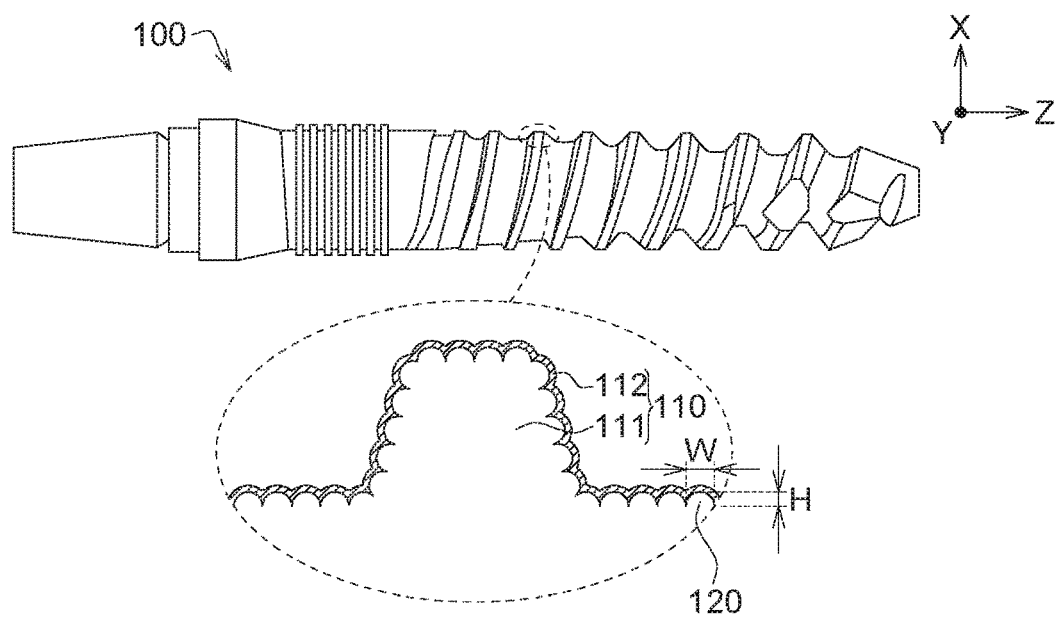
FIG. 1 is a diagram of a bone implant according to an embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

FIG. 1 is a diagram of a bone implant 100 according to an embodiment of the present disclosure. The bone implant 100 may be implanted into a human bone or an animal bone, such as an alveolar bone, a spine or other species of bones which need to be fixed by the bone implant. The bone implant 100 includes an implant body 110 and a plurality of microstructures 120.

The implant body 110 may be a pillar-shaped structure. The implant body 110 may have screws for being labour-savingly screwed to the bone. In another embodiment, the implant body 110 may have no screw. In an embodiment, the implant body 110 may be made of metal including titanium or an alloy including titanium, such as TiAlV (titanium aluminum vanadium) alloy. Under the processing of the ultrafast laser, a portion of a surface of the material of the implant body 110 may be removed, and the remained material forms a plurality of microstructures 120, and the material of the implant body 110 includes an inner layer 111 and an outer layer 112, wherein the inner layer 111 is made of titanium metal or titanium alloy, and the outer layer 112 is a titanium dioxide film that is an oxidization layer of the material of the inner layer 111 of the implant body 110.

The microstructures 120 are formed on the surface of the implant body 110. Each microstructure 120 has a height H and a weight W, wherein the weight W is less than 2 micrometers, and the height H is less than 1 micrometer. Under such design, a surface area of the microstructure 120 may be increased, and accordingly the bone implant 100 has superhydrophilicity. In an embodiment, the implant body 110 may be made of $Ti_6Al_4V$, wherein the $Ti_6Al_4V$ may consist of, for example, about 6% Al, about 4% V, up to about 0.25% iron, up to 0.2% oxygen and the others may be Ti. Since the size design of the microstructure 120 (the width ranges between 0.1 micrometers and 1 micrometer, and the height is less than 1 micrometer), the contact angle of water drop on the implant body 110 is equal to or less than 6 degrees, and accordingly the microstructures 120 has superhydrophilicity.

In contrast, if the weight W of each microstructure 120 is larger than 2 micrometers and/or the height H of each microstructure 120 is larger than 1 micrometer, the contact angle of water drop on the implant body 110 is larger than 120 degrees. The contact angle of water drop on the implant body 110 is much larger than 6 degrees Due to the size design of the microstructures 120 of the present disclosure, the microstructures 120 can provide cells with a quality growing space, such that it is easy for the cells to grow and differentiate. In addition, due to the size design of the microstructures 120 of the present disclosure, the microstructures 120 vary in a small size range (such as nanometer scale) even if some microstructures 120 have large variations in size, and accordingly the large microstructures 120 do not unduly affect the growth and differentiation of the cells.

In an embodiment, the microstructures 120 may be formed by ultrafast laser light having infrared wavelength, and accordingly the microstructures 120 may be formed in micrometer dimension, nanometer dimension or combination thereof. Since the microstructures 120 may be formed by the ultrafast laser light, the microstructures 120 may be arranged in a regular pattern, and accordingly it is conducive to helping the cells to climb the bone implant 100 and uniformly grow. Due to the microstructures 120 are regularly arranged, the arithmetical mean deviation (Ra) of the implant body 110 of the microstructures 120 is less than 1 micrometer.

The width W of the microstructure 120 may range between 0.1 micrometers and 2 micrometers. The width W depends on the wavelength of the ultrafast laser light, refraction index of the implant body 110 and an included angle between an incidence direction of the ultrafast laser light and a normal direction of material surface, as formulated in equation (1) below.

$$\Lambda_1 = \frac{\lambda}{n(1 \pm \sin\theta)} \quad (1)$$

In equation (1), the $\Lambda_1$ represents a period of the microstructures 120, $\lambda$ represents the wavelength (nm) of the ultrafast laser light, n represents the refraction index of the implant body 110, and $\theta$ represents the included angle between the incidence direction of the ultrafast laser light and the normal direction of the surface of the implant body 110. The period $\Lambda_1$ representing an interval between the adjacent two microstructures 120 is substantially equal to the width W1, and thus the period $\Lambda_1$ of the equation (1) may represent the width W.

The implant body 110 is made of a material including titanium. As a result, under the processing of the ultrafast laser light, the outer layer 112 of the implant body 110 forms the titanium dioxide film, and accordingly an extra process for the dioxide film is not required. The titanium dioxide film may provide the cells with growing environment, and accordingly it is easy for the cells to grow, climb and differentiate for speeding up the growing of the cells. The bone cells tend to growing on the titanium dioxide film, and the growing speed may be increased. In addition, the titanium dioxide film has a thickness less than or equal to 1 micrometer, such as a range between 0.002 micrometers and 1 micrometer.

Figure 2:
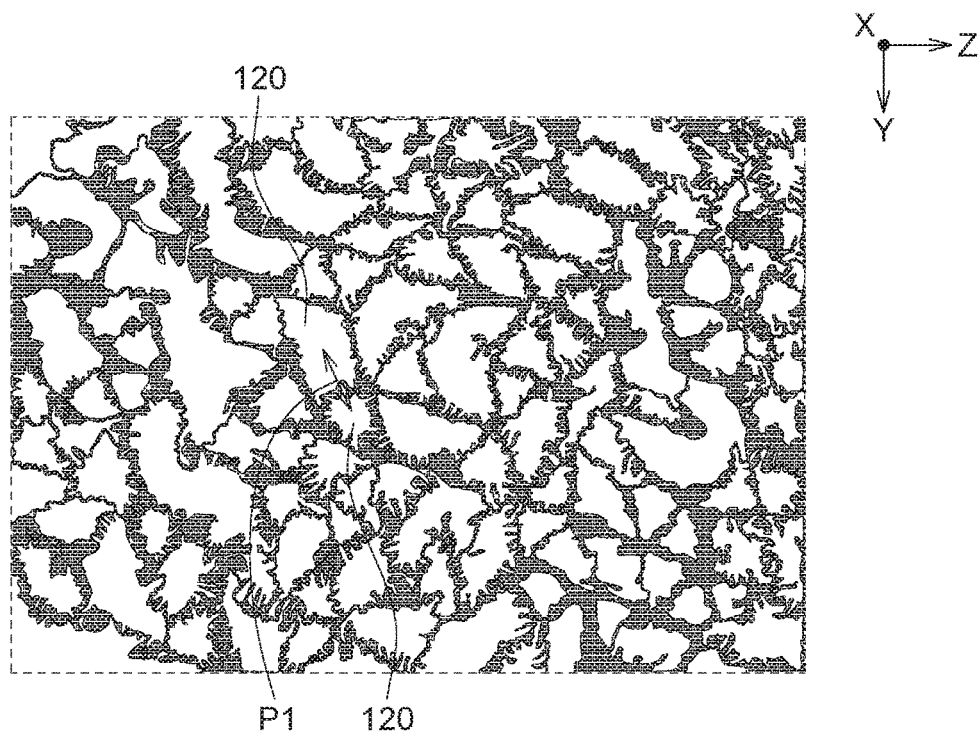
FIG. 2 is a local top view of the microstructures according to an embodiment of the present disclosure.

FIG. 2 is a local top view of the microstructures 120 according to an embodiment of the present disclosure. As shown in FIGS. 1 and 2, each microstructure 120 is a pillar-shaped structure that projects toward a radial direction (for example, X direction of FIG. 2) of the implant body 110. Since the process of the ultrafast laser light, the microstructures 120 are substantially arranged in a regular pattern. For example, the interval P1 between the adjacent two microstructures 120 is less than 2 micrometers. Due to the interval P1 between the adjacent two microstructures 120 being tiny, the microstructures 120 vary in a small size range (such as nanometer) even if some microstructures 120 have large variations in size, and accordingly the large microstructures 120 do not unduly affect the growth and differentiation of the cells. That is, since the interval P1 between the adjacent two microstructures 120 is tiny, it can provide the cells with the quality growing space, such that it is easy for the cells to grow and differentiate.

Figure 3:
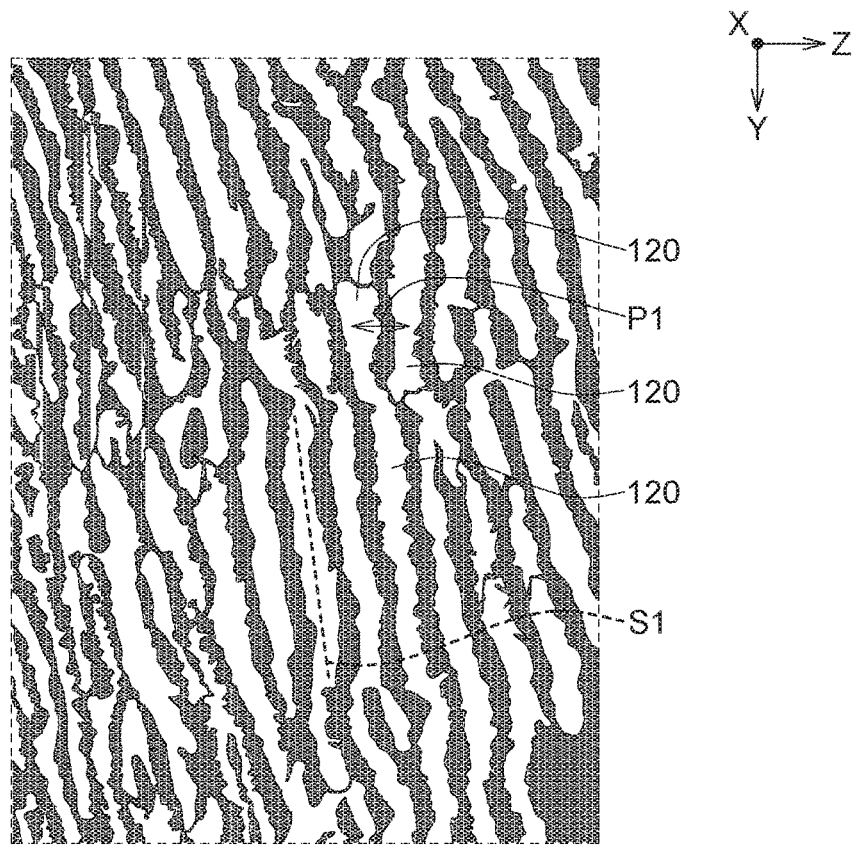
FIG. 3 is a local top view of the microstructures according to an embodiment of the present disclosure.

FIG. 3 is a local top view of the microstructures 120 according to an embodiment of the present disclosure. As shown in FIGS. 1 and 3, each microstructure 120 is a stripe-shaped structure that projects toward the radial direction (for example, X direction of FIG. 3) of the implant body 110 and extends around an implanting direction Z of the implant body 110. In the present embodiment, an include angle between the extension direction 51 of the microstructure 120 and the implanting direction Z of the implant body 110 is about 90 degrees. In another embodiment, the include angle between the extension direction 51 of the microstructure 120 and the implanting direction Z of the implant body 110 may range between 0 and 90 degrees.

Similarly, since the process of the ultrafast laser light, the microstructures 120 of FIG. 3 are substantially arranged in a regular pattern. For example, the interval P1 between the adjacent two microstructures 120 is less than 2 micrometers. Due to the interval P1 between the adjacent two microstructures 120 being tiny, the microstructures 120 vary in a small size range (such as nanometer scale) even if some microstructures 120 have large variations in size, and accordingly the large microstructures 120 do not unduly affect the growth and differentiation of the cells. That is, since the interval P1 between the adjacent two microstructures 120 is tiny, it can provide the cells with the quality growing space, such that it is easy for the cells to grow and differentiate.

Figure 4:
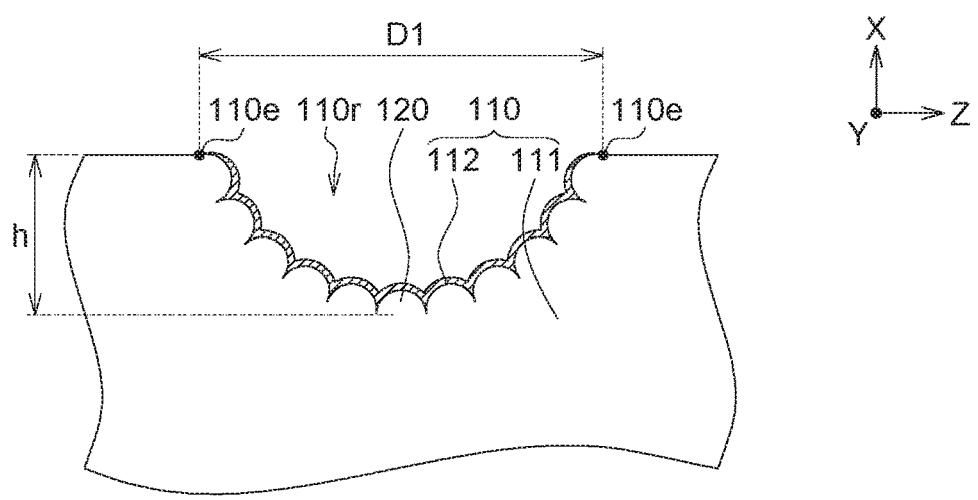
FIG. 4 is a local diagram of the microstructures according to an embodiment of the present disclosure.

FIG. 4 is a local diagram of the microstructures 120 according to an embodiment of the present disclosure. As shown in FIGS. 1 and 4, the implant body 110 has at least one recess 110r within which the microstructures 120 are formed. In an embodiment, the recess 110r may be formed by the ultrafast laser light gasifying a portion material of the implant body 110; in the meantime, the microstructures 120 are formed on an inner sidewall of the recess 110r. A diameter D1 of the recess 110r may depend on a diameter of the ultrafast laser light. In an embodiment, the diameter D1 of the recess 110r is, for example, 20 micrometers, less or larger than 20 micrometers. A depth h of the recess 110r may depend on energy and/or processing time of the ultrafast laser light and range between 0.005 micrometers and 1 micrometer. In another embodiment, the depth h of the recess 110r is unapparent. For example, the depth h approaches 0.005 micrometers.

As shown in FIG. 4, due to pulse duration of the ultrafast laser light is shorter than time of electron transmitting heat to an edge 110r of the recess 110r, and accordingly it prevents a burr from being formed on the edge 110e of the recess 110r. For example, in the present embodiment, as shown in FIG. 4, the edge 110e of the recess 110r do not form the burr projecting toward the radial direction (for example, X direction).

Figure 5A:
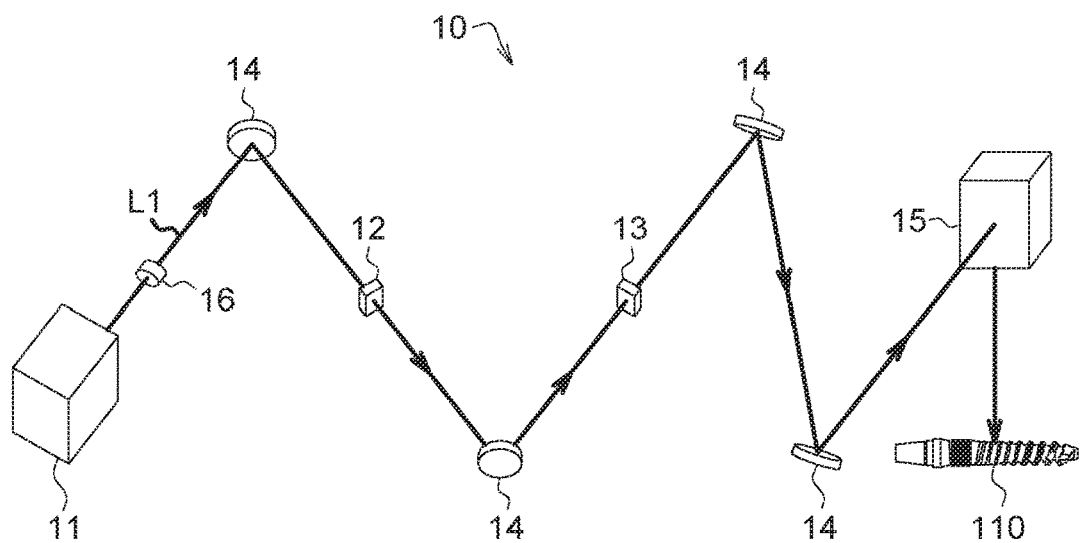
FIGS. 5A to 5B are process diagrams of the bone implant of FIG. 1.
Figure 5B:
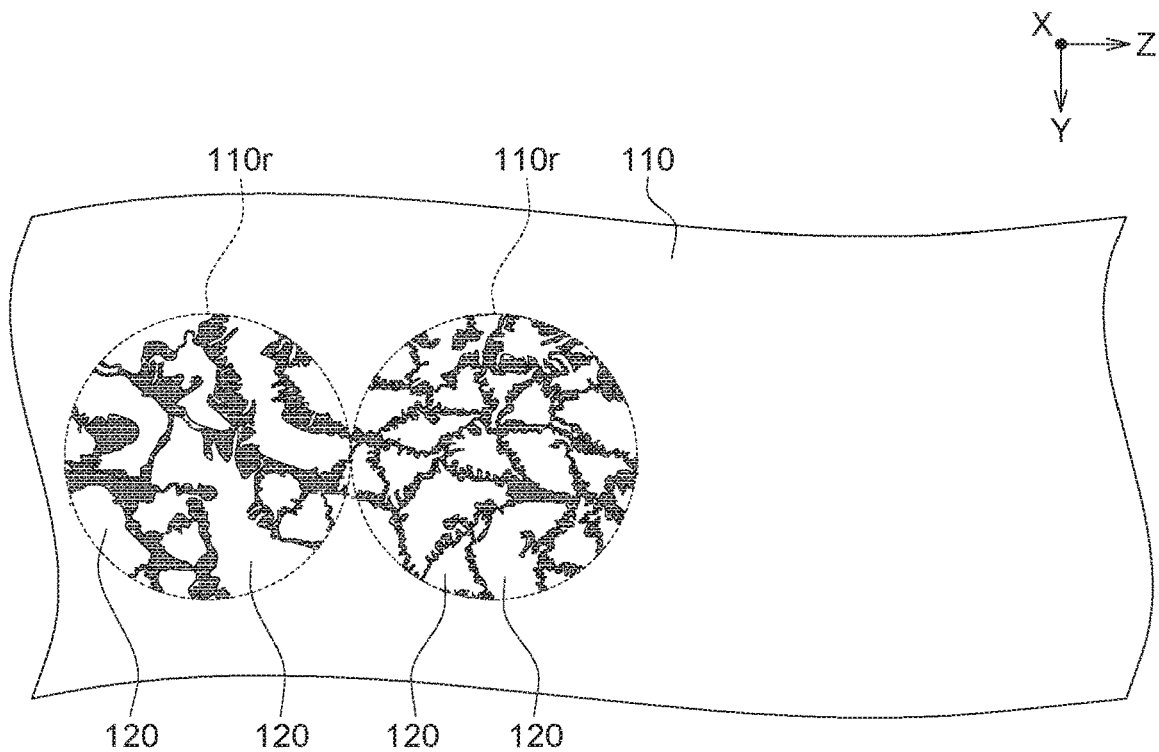

FIGS. 5A to 5B are process diagrams of the bone implant 100 of FIG. 1.

As shown in FIG. 5A, the implant body 110 is provided, wherein the implant body 110 is made of metal comprising titanium or an alloy comprising titanium.

As shown in FIG. 5A, a processing apparatus 10 is provided. The processing apparatus 10 includes an ultrafast laser source 11, a first wave plate 12, a second wave plate 13, a plurality of reflective mirror 14, a processing head 15 and a beam expander 16. The ultrafast laser source 11 may emit the ultrafast laser light L1. The ultrafast laser light L1 is incident to the processing head 15 through the first wave plate 12 and the second wave plate 13, and the processing head 15 focus the energy of the laser on the surface of the implant body 110 for forming the microstructures 120 on the implant body 110. The reflective mirrors 14 may change an optical path of the ultrafast laser light L1, such that the ultrafast laser light L1 may be successfully emitted to the processing head 15 through the first wave plate 12 and the second wave plate 13. The beam expander 16 is located between the ultrafast laser source 11 and the reflective mirrors 14 and configured to expand the diameter of the ultrafast laser light L1.

The first wave plate 12 is, for example, a half wave plate. The first wave plate 12 may control the energy of the ultrafast laser light L1 to control the height H of the microstructure 120 and/or the thickness of the titanium dioxide film.

The second wave plate 13 is, for example, a quarter wave plate. The second wave plate 13 may control the microstructure 120 to be shaped as the shape as shown in FIG. 2, FIG. 3 or other shape. For example, through rotating an orientation of the second wave plate 13 to control a direction of a fast axis of the second wave plate 13, the ultrafast laser light L1 passing through the second wave plate 13 may be transformed to linearly polarized light, circularly polarized light or elliptically polarized light for forming the microstructure 120 having different shapes and/or extension ways.

In addition, the pulse duration of the ultrafast laser light L1 may be equal to or less than $10^{-12}$ seconds to $10^{-15}$ seconds, the repetition rate of the ultrafast laser light L1 may be less than or equal to 10 MHz, and the wavelength of the ultrafast laser light L1 may range between that of ultraviolet and that of infrared. The laser threshold of the ultrafast laser light L1 may be less than or equal to 5 Joule/cm$^2$ (J/cm$^2$) and/or the pulse number of effective shots of the ultrafast laser light L1 may be equal to or less than 300 shots for forming the microstructures 120 of the present embodiments of the present disclosure. The term "the pulse number of the effective shots" means the implant body 110 receives the number of the laser pulses per unit area. The pulse number of the effective shots depends on the height H of the microstructure 120. For example, if the pulse number of the effective shots is more than 300 shots, the height H of the microstructure 120 is larger than 1 micrometer. In contrast, if the pulse number of the effective shots is less than 300 shots, the height H of the microstructure 120 is less than 1 micrometer. The laser threshold of the ultrafast laser light L1 means a ratio of the working (joule) of the ultrafast laser light L1 to an area (square centimeter, cm$^2$) of the diameter of the light beam.

As shown in FIG. 5, after the recess 110r (selectively) is formed on the outer surface of the implant body 110 and a plurality of the microstructures 120 are formed on the inner sidewall of the recess 110r by the ultrafast laser light L1, another recess 110r (selectively) may be formed on the outer surface of the implant body 110 and a plurality of the microstructures 120 are formed on the inner sidewall of the another recess 110r along a direction of the implant body 110, wherein the direction is, for example, the implanting direction Z of the implant body 110, the direction (for example, Y direction of FIG. 5) around the implanting direction Z or other arbitrary direction. The number of the recesses 110r or the number of the microstructures 120 may depend on demand and/or requirement, and it is not limited to this embodiment. In addition, in another embodiment, under the control of the pulse duration, the repetition rate, the wavelength and/or the laser threshold of the ultrafast laser light L1, the recess 110r is apparently formed on the implant body 110 or the formed recess 110r is unapparent.

As described above, through the ultrafast laser light passing through the processing apparatus which have polarization property, the microstructures may be formed on the implant body, wherein the microstructure has micro dimension. For example, the width of the microstructure is less than 2 micrometers and the height of the microstructure is less than 1 micrometer, and accordingly the microstructures have superhydrophilicity that is conducive to being implanted into the bone of living organism. In another embodiment, in the same process of the ultrafast laser light, the microstructures and the titanium dioxide film may be formed in the meantime. The titanium dioxide film may provide the cells with growing space, such that it is easy for the cells to climb and differentiate for increasing the growing speed of the cells. Due to the design of the microstructures and/or the titanium dioxide film, the bone implant of the embodiment of the present disclosure may be tested and verified by the ISO 10993. In addition, according to the result of test, after the bone implant of the embodiment of the present disclosure is implanted into the bone of the living organism for three months, osseointegration growth rate can reach 94%. Compared to this, the osseointegration growth rate of the bone implant formed by way of anode surface treatment is only about 77% or higher than 17%.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A manufacturing method of a bone implant, comprising:
    providing an implant body, wherein the implant body is made of metal comprising titanium or an alloy comprising titanium;
    providing a processing apparatus, wherein the processing apparatus comprises an ultrafast laser source, a first wave plate and a second wave plate; and
    emitting an ultrafast laser light by the ultrafast laser source through the first wave plate and the second wave plate to be incident to the implant body to form a plurality of microstructures and a titanium dioxide film, wherein each microstructure has a height and a weight, the weight is less than 2 micrometers, and the height is less than 1 micrometer.

2. The manufacturing method according to claim 1, wherein a laser threshold of the ultrafast laser light incident to the implant body is less than 5 joule/cm2.

3. The manufacturing method according to claim 1, wherein the ultrafast laser light emitted by the ultrafast laser source has a pulse number of effective shots that [[of the ultrafast laser light]] is less than 300 shots.

4. The manufacturing method according to claim 1, wherein the first wave plate is a half wave plate.

5. The manufacturing method according to claim 1, wherein the second wave plate is a quarter wave plate.

* * * * *